United States Patent
Panz

(10) Patent No.: US 6,564,463 B1
(45) Date of Patent: May 20, 2003

(54) APPARATUS FOR MEASURING HAIR LENGTH

(76) Inventor: Ulla-Monika Panz, Hauptstrasse 57, D-71566 Althütte (DE)

( * ) Notice: Subject to any disclaimer, the term of this patent is extended or adjusted under 35 U.S.C. 154(b) by 0 days.

(21) Appl. No.: 09/787,791

(22) PCT Filed: Sep. 18, 1999

(86) PCT No.: PCT/EP99/06926

§ 371 (c)(1),
(2), (4) Date: Jul. 2, 2001

(87) PCT Pub. No.: WO00/18297

PCT Pub. Date: Apr. 6, 2000

(30) Foreign Application Priority Data

Sep. 25, 1998 (DE) .......................... 198 44 042

(51) Int. Cl.⁷ ............................................. A45D 24/36
(52) U.S. Cl. ............................ 33/512; 33/759; 132/214
(58) Field of Search ................... 33/511, 512, 514.1, 33/514.2, 755, 758, 759, 1 BB, 418, 422, 452, 465, 760; 446/27; 132/213, 214

(56) References Cited

U.S. PATENT DOCUMENTS

| 456,286 | A | * | 7/1891 | Denzer | 223/25 |
|---|---|---|---|---|---|
| 1,091,372 | A | * | 3/1914 | Mickelson | 132/214 |
| 1,322,395 | A | * | 11/1919 | Baker | 33/512 |
| 1,355,038 | A | * | 10/1920 | Ford | 132/214 |
| 1,507,168 | A | * | 9/1924 | Goodrum | 132/213 |
| 1,508,811 | A | * | 9/1924 | Perkins-Kelly | 33/514.2 |
| 1,537,783 | A | * | 5/1925 | Olson | 132/214 |
| 2,684,534 | A | * | 7/1954 | Ljungberg | 33/766 |
| 2,749,555 | A | * | 6/1956 | Oliveira | 40/329 |
| 2,786,477 | A | * | 3/1957 | Cohen | 132/214 |
| 3,453,771 | A | * | 7/1969 | Barkhordar | 446/27 |
| 3,613,294 | A | * | 10/1971 | Graham | 446/27 |
| 3,834,030 | A | * | 9/1974 | Hanson | 33/759 |
| 4,106,515 | A | * | 8/1978 | Miller | 132/214 |
| 4,428,124 | A | * | 1/1984 | Asakura | 33/334 |
| 5,027,992 | A | * | 7/1991 | Murray, III | 224/181 |
| 5,427,383 | A | * | 6/1995 | Viens | 473/490 |

* cited by examiner

Primary Examiner—Christopher W. Fulton
Assistant Examiner—R. Alexander Smith
(74) Attorney, Agent, or Firm—Pendorf & Cutliff

(57) ABSTRACT

The invention relates to a device for measuring the length of the hair and/or the portions of the face of an individual being examined. In order to enable precise and reproducible measurement, the invention provides a support that can be placed on the head of a person and having a flexible measuring element disposed in the area of the top or crown of the head. Said support consists of two flexible support brackets (10, 12) disposed perpendicularly relative to each other, on the crossing. point (16) of which the measuring element (14) preferably in the form of a measuring tape is attached in a freely rotational manner.

10 Claims, 1 Drawing Sheet

APPARATUS FOR MEASURING HAIR LENGTH

BACKGROUND OF THE INVENTION

Field of the Invention

The invention concerns a device for measuring the length and the hair and/or the facial proportions of a person being examined.

Research has shown that the proportions of the face and the body of a subject harmonize particularly well with certain lengths of hair, while other hair lengths achieve an unproportioned impression. A barber or stylist has had in the past to rely on his intuition when working with hair, in order to create for the respective "type" of subject the appropriate hair cut.

SUMMARY OF THE INVENTION

The task of the invention is thus comprised of providing a device with which the length of the hair and the facial proportions of a subject can be determined precisely and reproducibly.

The invention is based above all on the idea, that the length of the hair and the facial proportions can be particularly precisely and reproducibly measured when the measurement begins starting from a predefined reference point. In accordance with the invention there is thus provided a support that can be placed on the top of the head of a person, the support having a flexible measuring element disposed in the area of the top or crown of the head. The support is comprised preferably of a first frame piece extending essentially in the longitudinal direction of the head, and a second frame piece oriented perpendicularly to the first frame piece and comprised of an elastic material, the frame pieces crossing each other at the height of the crown of the head. In order to make possible a comfortable seating of the support upon the head, the frame pieces should conform to the contour of the head.

The first frame piece extending in the longitudinal direction of the head preferably extends from the nape of the neck to the forehead, while the second frame piece oriented perpendicularly thereto ends on the sides of the head above the ears. The measuring element is preferably provided at the crossing points of the frame pieces.

The hair length and the facial proportions of the subject can be determined in particularly and precise manner, when the measuring device is a measuring band preferably with centimeter and/or millimeter gradations.

The support is preferably comprised of shaped plastic or metal strips, which are connected to each other via an adhesive or rivet connection. In order to make possible the measurement in any desired direction, the measuring element should be secured freely rotatable around the vertical axis o the support.

BRIEF DESCRIPTION OF THE DRAWING

In the following, the invention will be described in greater detail on the basis of the illustrative embodiment shown schematically in the figure. There is shown:

FIG. 1b a side view of the support of the device according to, FIG. 1a; and

FIG. 1c a back view of the support of the device according to FIG. 1a.

DETAILED DESCRIPTION OF THE INVENTION

Figure 1A:
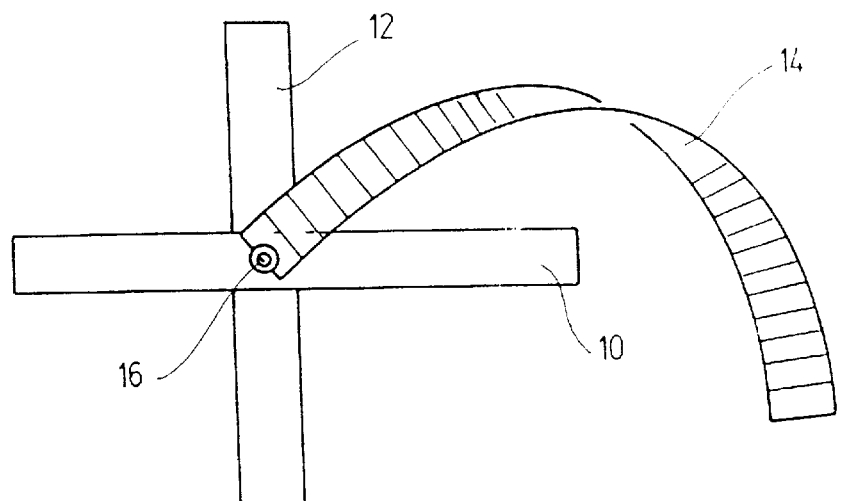
FIG. 1a a view from above upon the inventive device.
Figure 1B:
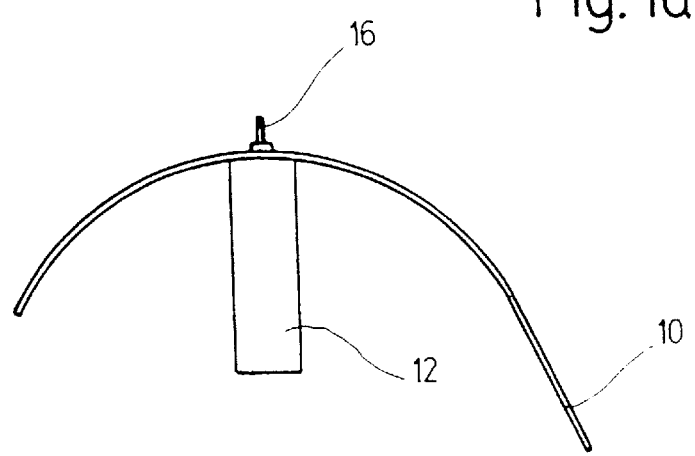
Figure 1C:
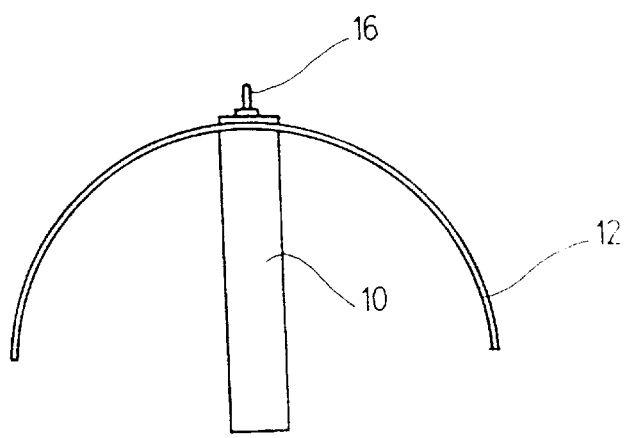

The device schematically represented in the figures is used for determining the hair length and/or the facial proportions of a subject. The device is comprised essentially of a support comprised of two frame pieces 10, 12, and a measuring element 14 shown as a tape measure, wherein the frame pieces 10, 12 cross each other at right angles and are connected to each other via adhesive or a rivet connection. The frame pieces are comprised of elastic plastic or metal, so that the support can be seated upon the head of the subject in the manner of a helmet and remains securely in position, without applying an uncomfortable amount of pressure. The level of comfort is increased by pre-forming the frame pieces 10, 12 to conform anatomically. The longitudinally extending frame piece 10 extends from the forehead to the nape of the neck while the frame piece 12 running perpendicular thereto ends on both sides of the head above the ears.

The crossing point of the frame pieces 10, 12 is situated in the area of the crown of the head. At this point the tape measure 14 is also secured on a pin 16 freely rotatable about the vertical axis. The pin 16 or, as the case may be, the crown height forms the reference point, from which the hair length of the subject as well as the facial proportions can be measured. Research has shown, that for particular facial proportions, that is, spacing of the eyes, the nose, the mouth and the chin from each other or, as the case may be, from the reference point 16, the optimal, that is, the particularly positive total impression producing hair length can be calculated according to a mathematical process.

In summary the following can be concluded: The invention relates to a device for measuring the length of the hair and/or the portions of the face of an individual being examined. In order to enable precise and reproducible measurement, the invention provides a support that can be placed on the head of a person and having a flexible measuring element disposed in the area of the top or crown of the head. The support consists of two flexible support brackets (10, 12) disposed perpendicularly relative to each other, on the crossing point (16) of which a measuring element (14) in the form of a measuring tape is fixed in a freely rotational manner.

What is claimed is:

1. A device for measuring at least one of a length of the hair of the head and facial proportions of a subject, the device comprising:

a support (10, 12) adapted to be seatable upon the head of said subject, the support comprising a first frame piece (10) which extends along the longitudinal direction of the head and a second frame piece (12) oriented perpendicularly to said first frame piece, wherein the first frame piece and the second frame piece cross each other at a crossing point, the first frame piece having a length different from a length of the second frame piece; and a flexible measuring element (14) pivotally connected to the crossing point.

2. A device as in claim 1, wherein said support is comprised of an elastic material.

3. A device according to claim 1, wherein the crossing point is adapted to be located at the crown of the head when said support is seated on the head of said subject.

4. A device according to claim 1, wherein the first frame piece (10) is adapted for extending in the longitudinal direction of the head from the nape of the neck to the forehead.

5. A device according to claim 1, wherein said second frame piece (12) is adapted to end on both sides of the head above the ears.

6. A device according to claim 1, wherein the measuring element (14) is a measuring tape with centimeter gradations.

7. A device according to claim 1, wherein said support (10, 12) is comprised of pre-formed plastic or metal strips.

8. A device according to claim 7, wherein the plastic or metal strips are connected to each other via a connection selected from adhesive connection and rivet connection.

9. A device according to claim 1, wherein the measuring element (14) is secured to the support and is freely rotatable about an axis.

10. A device for measuring at least one of a length of the hair of the head and facial proportions of a subject, the device comprising:

a support (10, 12) adapted to be seatable upon the head of said subject, the support comprising a first frame piece (10) which extends along the longitudinal direction of the head and a second frame piece (12) oriented perpendicularly to said first frame piece, wherein the first frame piece and the second frame piece cross each other at a crossing point, the first frame piece having a length different from a length of the second frame piece; and a flexible measuring element (14) pivotally connected to the crossing point;

wherein the frame pieces (10, 12) are shaped to conform to the contour of the head.

* * * * *